United States Patent [19]

Behan et al.

[11] Patent Number: 5,501,805
[45] Date of Patent: Mar. 26, 1996

[54] FRAGRANCE COMPOSITIONS AND THEIR USE IN DETERGENT PRODUCTS

[75] Inventors: John M. Behan, Ashford; Christopher F. Clements, Folkestone, both of England

[73] Assignee: Lever Brothers Company, Division of Conopco, Inc., New York, N.Y.

[21] Appl. No.: 428,398

[22] Filed: Apr. 25, 1995

Related U.S. Application Data

[60] Continuation of Ser. No. 89,154, Jul. 8, 1993, abandoned, which is a division of Ser. No. 697,918, May 1, 1991, abandoned, which is a continuation-in-part of Ser. No. 539,636, Jun. 18, 1990, abandoned.

[30] Foreign Application Priority Data

Jun. 19, 1989 [GB] United Kingdom .................. 8914055

[51] Int. Cl.$^6$ ................................ C11D 3/50; C11B 9/00; D06M 13/00
[52] U.S. Cl. ...................... 252/8.6; 252/8.8; 252/174.11; 512/2; 512/20
[58] Field of Search ................................ 252/174.11, 8.6, 252/8.8, 20, 2

[56] References Cited

U.S. PATENT DOCUMENTS

| | | | |
|---|---|---|---|
| 4,134,838 | 1/1979 | Hooper et al. | 252/8.8 |
| 4,288,341 | 9/1981 | Hooper et al. | 252/107 |
| 4,289,641 | 9/1981 | Hooper et al. | 252/96 |
| 4,289,644 | 9/1981 | Steinhauer et al. | 252/127 |
| 4,292,192 | 9/1981 | Hooper et al. | 252/132 |
| 4,304,679 | 12/1981 | Hooper et al. | 252/106 |
| 4,322,308 | 3/1982 | Hooper et al. | 252/107 |
| 4,326,967 | 4/1982 | Melville | 252/8.8 |
| 4,337,180 | 6/1982 | Kiwala | 252/174.11 |
| 4,343,783 | 8/1982 | Hooper et al. | 424/28 |
| 4,347,153 | 8/1982 | Hooper et al. | 252/174.25 |
| 4,352,748 | 10/1982 | Traas et al. | 252/174.11 |
| 4,469,848 | 9/1984 | Hooper et al. | 252/106 |
| 4,511,495 | 4/1985 | Melville | 252/522 |
| 4,515,705 | 5/1985 | Moeddel | 252/174.12 |
| 4,579,677 | 4/1986 | Hooper et al. | 252/95 |
| 4,650,603 | 3/1987 | Sprecker | 252/522 R |
| 4,663,068 | 5/1987 | Hagemann et al. | 252/99 |
| 4,698,180 | 10/1987 | Pavlin | 568/665 |
| 4,840,792 | 6/1989 | Joulain et al. | 424/76.1 |
| 4,915,866 | 4/1990 | Mookherjee | 252/174.11 |
| 4,923,631 | 5/1990 | Sins et al. | 252/186.42 |
| 4,929,599 | 5/1990 | Giersch et al. | 252/174.11 |

FOREIGN PATENT DOCUMENTS

| | | |
|---|---|---|
| 3172 | 7/1979 | European Pat. Off. . |
| 3171 | 7/1979 | European Pat. Off. . |
| 5618 | 11/1979 | European Pat. Off. . |
| 147191 | 7/1985 | European Pat. Off. . |
| 299561 | 1/1989 | European Pat. Off. . |
| 545556 | 6/1993 | European Pat. Off. . |
| 1530436 | 4/1966 | France . |
| 57-85900 | 5/1982 | Japan . |
| 57-85898 | 5/1982 | Japan . |
| 1472536 | 5/1977 | United Kingdom . |

OTHER PUBLICATIONS

Woodworth et al., *Experimental Psychology*, Editors Kling & Riggs (1971), pp. 73–79 (no month available).

Malodor Control–A Review, *Perfumer and Flavourist*, V. 11, No. 3–Jun./Jul. 1986.

Seventh Detergent Congress in Barcelona, Spain in Mar. 1976, VII Jornadas del Comite Espanol de la Detergencia on pp. 201–228, English translation included.

*Primary Examiner*—Paul Lieberman
*Assistant Examiner*—Erin M. Harriman
*Attorney, Agent, or Firm*—A. Kate Huffman

[57] ABSTRACT

Compositions of fragrance materials having an Odour Intensity Index of less than 110, and a Malodour Reduction Value of at least 0.25 or an Odour Reduction Value of at least 0.25, can be used as fragrance compositions in detergent powders, detergent liquids, soap or detergent bars or pastes, fabric-conditioning compositions in liquid or solid form, or personal body deodorant compositions, to confer deodorant effects in use even though they have in themselves a low or imperceptible level of fragrance (Odour Intensity Index).

11 Claims, No Drawings

FRAGRANCE COMPOSITIONS AND THEIR USE IN DETERGENT PRODUCTS

This is a continuation application of Ser. No. 08/089,154, filed Jul. 8, 1993 now abandoned which in turn is a divisional application of 07/697,918, filed on May 1, 1991 now abandoned which is a continuation-in-part of 07/539,636 filed Jun. 18, 1990 now abandoned.

This invention relates to compositions of fragrance materials and their use in detergent products.

In particular embodiments, the invention relates to combinations of such fragrance compositions with detergent powders, e.g. granulates, with liquids, especially for example those intended for fabric-washing, with soap and detergent bars and pastes, with fabric-conditioning compositions e.g. in liquid or solid (sheet) form, and with personal body deodorant compositions, e.g. underarm deodorants.

PRIOR ART

EP 0 003 171 and EP 0 003 172 (Unilever) and U.S. Pat. No. 4,304,679 (Lever) (and the references cited therein) give extensive known examples of perfumery compositions especially with reference to their use in detergents.

EP 0 003 171 and EP 003 172 also disclose compositions in which the perfume compositions have a deodorant effect when they are used.

Further examples of perfumery compositions, as well as their application to enzyme-containing detergents, are given in JP 57-85898 and JP 57-85900 (Lion Corp), and in U.S. Pat. No. 4,515,705 (Procter & Gamble).

EP 0 147 191 (Unilever) gives further examples of perfumery compositions, having not only deodorant effect but also stability in the presence of bleaching compositions.

It is also proposed in GB 1 589 866 to incorporate 0.3–3% of ester of citrate or acetylcitrate (eg. triethyl citrate) as a deodorant in a soap bar.

SUMMARY OF THE PRESENT INVENTION

It has surprisingly been found that certain compositions of fragrance materials can confer deodorant effects in use even though they have in themselves a low or imperceptible level of fragrance (low odour intensity). This is of advantage in many applications where an intense fragrance is not desired, while a deodorant effect is to be welcomed.

According to an aspect of the invention, there is provided a composition of fragrance materials having (a) an Odour Intensity Index of less than about 110, (often less than about 105, and preferably less than about 100), when tested according to an Odour Intensity Test as described below, and (b) a Malodour Reduction Value of at least about 0.25, preferably, at least about 0.5, when tested according to the test procedure set out in European Patent Application No. 0 147 191 or an Odour Reduction Value of about 0.25, preferably at least about 0.5, when tested according to the test procedure set out in European Patent Application No. 0 003 172, both of which specifications are hereby incorporated herein by reference.

It is understood that in this specification, expressions such as 'perfume' and 'fragrance' extend to compositions of which the odour intensity may be so low as to be imperceptible in use.

A suitable selection of examples of perfumery materials for incorporation into such compositions is for example provided in the Examples below. More generally, any of a wide range of perfumery materials may be incorporated into the compositions, provided that the basis of selection is such as to provide a deodorant effect, and the odour intensity index of the resulting composition is as defined above.

Extensive directions for the selection of materials in order to provide a deodorant effect are given for example in EP 0 147 191EP 0 003 172, and U.S. Pat. No. 4,304,679, all three incorporated herein by reference.

It is helpful if the bulk of the individual ingredients chosen for the composition also individually possess an Odour Intensity Index less than about 110, preferably less than about 100, or even lower. Small quantities of more intense materials may however be tolerated, e.g. for the purpose of adjusting the mild perfume note which may be given by the overall composition.

In a number of particular embodiments, the compositions can comprise at least 20% by weight of at least one musk. More preferred is at least 30% by weight of musk, e.g. at least 35% or at least 40%. Where one or more musks are present, either in these or in other amounts, they can usefully be selected from musks such as galaxolide (TM) (IFF) (in class 3 defined below) and/or Traseolide (TM) (Quest) (in class 4 defined below).

Galaxolide is 1,3,4,6,7,8-hexahydro-4,6,6,7,8,8-hexamethylcyclopenta- 2-benzopyran. Traseolide is 6-acetyl-1-isopropyl-2,3,3,5-tetramethylindane.

Other musks which may be used are as follows:

| Trademark or Trivial Name: | Generic name: |
|---|---|
| Ambrettolide | Cyclohexadecen-7-olide |
| Celestolide (IFF) | 4-Acetyl-6-tert-butyl-1,1-dimethylindane |
| Dihydroambrettolide | Cyclohexadecanolide |
| Ethylene brassylate | cyclo-1,13-ethylenedioxy-tridecan-1,13-dione |
| Exaltolide (F) | Cyclopentadecanolide |
| Exaltone (F) | Cyclopentadecanone |
| Moskene (GIV) | 1,1,3,3,5-Pentamethyl-4,6-dinitroindane |
| Musk ambrette | 2,4-dinitro-3-methyl-6-tert-butylanisole |
| Musk Ketone | 4-tert-butyl-3,5-dinitro-2,6-dimethylacetophenone |
| Musk MC4 (SA) | Ethylene 1,12-dodecanedioate |
| Musk R1 (Q) | 11-Oxahexadecanolide |
| Musk tibetine | 2-tert-butyl-1,3-dinitro-4,5,6-trinitrobenzene |
| Musk xylol | 1-tert-butyl-3,5-dimethyl-2,4,6-trinitrobenzene |
| Phentolide (PFW) | 5-Acetyl-1,1,2,3,3,6 hexamethylindane |
| Tonalid (PFW) | 1,1,2,4,4,7-Hexamethyl-6-acetyl-1,2,3,4-tetrahydronaphthalene |
| Versalide (PFW) | 1,1,4,4-tetramethyl-6-acetyl-7-ethyl 1,2,3,4-tetrahydronaphthalene |

Suppliers indicated in brackets above arm as follows:

F=Firmenich

GIV=Givaudan

IFF=International Flavours & Fragrances

PFW=Polak's Frutal Works

SA=Soda Aromatics

Q=Quest International

The quantity of musk will generally not exceed 70%, more likely not exceed 60% by weight so that other (non-musk) perfume components provide at least 30% more likely at least 40% by weight of the perfume composition, Another category of ingredients present in many preferred compositions is salicylates of aliphatic or arylaliphatic alcohols containing at least three carbon atoms notably 3 to 10 carbon atoms, such salicylates preferably constitute at least 10% by weight of the composition of fragrance materials. Possible salicylates include;

amyl salicylate isoamyl salicylate isobutyl salicylate cis-3-hexenyl salicylate hexyl salicylate cyclohexyl salicylate benzyl salicylate phenylethyl salicylate propyl salicylate isopropyl salicylate.

According to another aspect of the invention, there is provided a detergent composition suitable for fabric-washing, comprising perfume ingredients which are (a) optionally at least about 0.02% preferably at least about 0.03% of musk, based on the weight of the detergent composition, (b) at least about 0.04% more usually et least about 0.07% of other perfume components, provided that the fragrance components (a) and (b) together have an Odour Intensity Index of less than 110, and provided that the aggregate of fragrance components together pass either of the odour reduction tests cited above.

The compositions of fragrance materials with low odour intensity may usefully be incorporated, according to this invention, in various detergent and personal care products in for example the following amounts (but without limitation):- usually about 0.1% or more; in fabric-washing compositions about 0.1–0.3%; in concentrated fabric-washing compositions up to about 0.8%: in fabric-conditioning liquids up to about 0.3%; in sheet-form fabric-conditioning solid preparations up to about 5%, especially 2% to 4%; in soap and detergent bars and pastes about 0.2–1.8%, especially 0.4 to 1%; in personal body deodorants about 0.1 to 3%, especially 0.4 to 1%.

In the light of the preferences indicated above a fabric conditioning liquid, a soap, a detergent bar or a personal body deodorant preferably comprises (a) at least about 0.02%, better about 0.03% of musk, based on the weight of the whole composition, and (b) at least 0.04% more usually at least about 0.07% of other perfume ingredients;

while a sheet-form fabric conditioning solid preferably comprises (a) at least about 0.4% by weight of musk, based on the weight of the whole composition and (b) at least about 0.8% of other perfume ingredients;

where in each instance the fragrance components (a) and (b) together have an Odour Intensity Index of less than 110.

Yet more preferably a soap or a personal body deodorant comprises at least about 0.08% by weight of musk (a) and at least about 0.15% of other perfume ingredients (b).

In certain embodiments, the invention also provides a deodorant perfume which comprises deodorant perfume components, eg. those which are judged to be stable in the presence of sodium perborate tetrahydrate and N,N,N'N'-tetraacetyl ethylenediamine (TAED) according to the Bleach Stability Test, as described in EP 0 147 191, the deodorant perfume having a Malodour Reduction Value of from 0.25 to 3.0 as measured by the Malodour Reduction Value Test, and also having the characteristic low odour intensity defined elsewhere herein.

Such deodorant perfumes can comprise from 50 to 100% by weight of (eg. bleach-stable) deodorant perfume components and from 0 to 50% by weight of further ingredients, said deodorant perfume components for example having a Lipoxidase-Inhibiting Capacity of at least 50% or a Raoult Variance Ratio of at least 1.1, and (where bleach stability is also desired) also being judged to be stable in the presence of sodium perborate tetrahydrate and N,N,N'N'-tetraacetyl ethylenediamine (TAED) according to the Bleach Stability Test, said components being allocated to one of six classes consisting of:

Class 1: Phenolic substances

Class 2: Essential oils, extracts, resins and synthetic oils (denoted "AB")

Class 3: Aldehydes and ketones

Class 4: Nitrogen-containing compounds and polycyclic compounds

Class 5: Esters

Class 6: Alcohols and ethers provided that where a deodorant perfume component can be assigned to more than one class, it is allocated to the class having the lower or lowest number; said components being so selected that:

a) the deodorant perfume contains at least five different components preferably at least one from each of class 1, 2 and 4;

b) the deodorant perfume contains components from at least four of the six classes; and c) any component present in the deodorant perfume at a concentration of less than 0.5% by weight of the said perfume is eliminated from the requirements of (a) and (b), said deodorant perfume having a Malodour Reduction Value of from 0.25 to 3.0 as measured by the Malodour Reduction Value Test which comprises the steps of:

i) selecting pieces of 100% bulked polyester sheet shirt fabric of 20 cm×20 cm;

ii) washing the selected pieces of fabric in a front-loading drum-type washing machine with a standard unperfumed washing powder containing the following ingredients:

|  | Parts by weight |
| --- | --- |
| Sodium dodecylbenzene sulphonate | 9 |
| $C_{13-15}$ alcohol 7EO | 4 |
| Sodium tripolyphosphate | 33 |
| Alkaline sodium silicate | 6 |
| Sodium carboxymethyl cellulose | 1 |
| Magnesium silicate | 1 |
| Ethylenediamine tetraacetic acid | 0.2 |
| Sodium sulphate | 15 |
| Water | 10.8 | iii) rinsing the washed pieces of fabric and drying them to provide "untreated" fabric;

iv) re-washing half of the "untreated" pieces of fabric in the washing machine with the standard washing powder to which has been added 0.2% by weight of a bleach-stable perfume under test, rinsing and re-drying to provide "treated" pieces of fabric;

v) inserting the "treated" and "untreated" pieces of fabric into clean polyester cotton shirts in the underarm region so that in each shirt, one underarm region receives a "treated" fabric insert and the other underarm region receives an "untreated" fabric insert in accordance with a statistical design;

vi) placing the shirts carrying the inserts on a panel of 40 Caucasian male subjects of age within the range of from 20 to 55 years (the subjects being chosen from those who develop axillary body malodour that is not unusually strong and who do not develop a stronger body malodour in one axilla compared with the other);

vii) assessing the body malodour of the fabric inserts after a period of five hours whereby three trained female assessors record the olfactory intensity of malodour on a 0 to 5 scale, 0 representing no odour and 5 representing very strong malodour, the strength of the odour in each instance being related for purposes of comparison to standard odours produced by aqueous solutions of isovaleric acid at different concentrations according to the following table:

| Score | Odour level | Conc. of aqueous isovaleric acid (ml/l) |
| --- | --- | --- |
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 | viii) calculating the average scores for both treated fabric and untreated fabric, and subtracting the average score of the treated fabric from the average score of the untreated fabric to arrive at the Malodour Reduction Value for the bleach-stable perfume, the bleach-stable perfume being designated a bleach-stable deodorant perfume when its Malodour Reduction Value is from 0.25 to 3.0;

the Bleach Stability Test comprising the steps of:

i) dosing a perfume material into the standard unperfumed washing powder and incubating the dosed powder at 20° C. in a sealed container for seven days;

ii) dividing the dosed powder into two portions and adding to each portion sodium perborate tetrahydrate together with either TAED granules or sodium sulphate (to act as an inert filler in place of TAED) to provide test and control formulations having the following constitution:

| | % w/w | |
| --- | --- | --- |
| | Test Powder | Control Powder |
| Standard unperfumed powder | 76 | 76 |
| Perfume material under test | 0.2 | 0.2 |
| Sodium perborate tetrahydrate | 13 | 13 |
| TAED granules (65% TAED) | 10.8 | — |
| Sodium sulphate | — | 10.8 | iii) incubating both test and control powders in sealed containers at 45° C. for a further seven days; and iv) assessing samples of the test and control powders according to a standard triangle test as described in "Manual on Sensory Testing Methods" published by the American Society for Testing and Materials (1969), using a panel of 20 assessors, who are instructed to judge by smell which of the three powder samples is the odd one out, the perfume material being designated a bleach-stable deodorant perfume component when the odd one out is correctly identified by no more than 9 of the 20 assessors.

Suitable TAED granules comprise TAED particles having a particle size distribution such that the majority of particles have sizes in a range from 75 to 150 µm, with not more than 50% smaller than 75 µm, not more than 20% smaller than 50 µm and not more than 20% larger then 150 µm, These particles are granulated with sodium tripolyphosphate and potassium tripolyphosphate to yield granules having a mean particle size of 700–900µm and a composition which is:

| | |
| --- | --- |
| TAED | 65% |
| sodium tripolyphosphate | 20% |
| potassium tripolyphosphate | 8% |
| water | 7% |

However, the exact proportions of TAED and other materials are not critical, neither is the nature of the inorganic adjunct.

Deodorant perfume components can be classified into six chemically defined classes. The perfume components may be described in terms of four categories, each of which is given below together with examples of components which are to be assigned to each category.

1) Single chemical compounds whether natural or synthetic, for example, hexyl salicylate: the majority of components are in this category.
2) Synthetic reaction products (products of reaction), mixtures of isomers and possibly homologues, for example, alpha-iso-methyl ionone.
3) Natural oils and extracts, for example, benzoin Siam resinoid.
4) Synthetic oils (eg. analogues of category 3): this category includes materials that are not strict analogues of natural oils but are materials that result from attempts to copy or improve upon certain natural oils, for example Bergamot AB 430.

Components of Categories (3) and (4) although often uncharacterised chemically are available commercially.

Where a material is supplied or used conventionally for convenience as a mixture, e.g. p-t-amyl cyclohexanone diluted with diethyl phthalate, for the purposes of this specification two components are present, so that use of 5% of a blend of 1 part of this ketone and 9 parts of diethylphthalate is represented as 0.5% of the ketone and 4.5% of diethyl phthalate.

It has been found advantageous in formulating the most effective deodorant perfumes to use components that, as well as satisfying the lipoxidase or morpholine tests satisfy further conditions. These conditions are:

i) there are at least five different components present conforming with the classification below;
ii) there are represented components from at least four different chemical classes (defined below);
iii) at least 50%, preferably at least 55% and most preferably from 60 to 100% by weight of the deodorant perfumes comprise deodorant perfume components conforming with the classification below;
iv) a component is not considered to contribute to the efficacy of the bleach-stable deodorant perfume if it is present in that perfume at a concentration of less than 0.5% by weight.

Each component should be allocated to one of six classes. These classes are: Class 1—Phenolic substances;

2—Essential oils, extracts, resins and synthetic oils (denoted "AB");

3—Aldehyde and ketones;

4—Nitrogen-containing compounds;

5—Esters;

6—Alcohols and ethers.

In assigning a component to a class, the following rules are to be observed. Where the component could be assigned to more than one class, the component is allocated to the class occurring first in the order given above: for example methyl anthranilate, which is a nitrogen-containing compound, is placed in Class 4, although as an ester it otherwise might have been allocated to Class 5. Similarly, ethyl salicylate, which is phenolic in character, is allocated to Class 1 instead of Class 5.

The following are examples of (also bleach-stable) deodorant perfume components that have either a Lipoxidase Inhibiting Capacity (LIC value) of at least 50% or a Raoult Variance Ratio (RVR value) of at least 1.1, and additionally have a Bleach Stability Test (BST) panel score of up to 9, indicating that they are judged to be bleach-stable. Their class, molecular weight (m), LIC and RVR values and BST panel scores as determined by the tests already described herein are also indicated.

The nomenclature adopted for the components listed below and for the perfume ingredients which appear in the perfume formulations of Examples 1 to 7 is, so far as is possible, that employed by Steffen Arctander in "Perfume and Flavour Chemicals (Aroma Chemicals)" Volume I and II (1969) and the "Perfume and Flavour Chemicals (Aroma Chemicals)" Volume I and II (1969) and the "Perfume & Flavour Materials of Natural Origin" (1960) by the same author. Where a component or ingredient is not described by Arctander, then either the chemical name is given or, where this is not known the perfumery house speciality code name is given. Note that synthetic oils denoted "AB" are available from Quest International Limited.

Specific examples of perfume components are:

| | LIC value | RVR value | m | BST panel score |
|---|---|---|---|---|
| Class 1 - Phenolic Substances | | | | |
| iso-Amyl salicylate | 95 | 1.24 | 208 | 9 |
| Carvacrol | 32 | 1.43 | 150 | 6 |
| Clove leaf oil | 79 | 1.43 | 164 | 5 |
| Ethyl salicylate | — | 1.19 | 194 | 7 |
| iso-Eugenol | 100 | 1.48 | 164 | 4 |
| Hexyl salicylate | 100 | — | 222 | 5 |
| Thyme oil red | 55 | 1.37 | 150 | 9 |
| Class 2 - Essential oils, extracts, resins and synthetic oils (denoted "AB") | | | | |
| Bergamot AB 430 | 58 | 0.97 | 175 | 7 |
| Geranium AB 76 | 26 | 1.29 | 154 | 6 |
| Rose AB 380 | 0 | 1.28 | 175 | 9 |
| Rose AB 409 | 35 | 1.34 | 175 | 8 |
| Class 3 - Aldehydes and ketones | | | | |
| 7-Acetyl-1,1,3,4,4,6-hexamethyl-tetrahydro-naphthalene | 100 | 1.03 | 258 | 8 |
| p-t-Amyl cyclohexanone | 50 | 1.10 | 182 | 8 |
| 2-n-Heptylcyclo-pentanone | 56 | 1.05 | 182 | 7 |
| α-iso-Methyl ionone | 100 | 1.13 | 206 | 7 |
| β-Methyl naphthyl ketone | 100 | 0.96 | 170 | 3 |
| Class 4 - Nitrogen-containing compounds | | | | |
| iso-Butyl quinoline | — | 1.10 | 185 | 5 |
| Methyl anthranilate | 69 | 1.20 | 151 | 6 |
| Class 5 - Esters | | | | |
| o-t-Butylcyclohexyl acetate | 52 | 1.08 | 198 | 8 |
| Diethyl phthalate | 79 | 1.20 | 222 | 4 |
| Nonanediol-1,3-diacetate | 33 | 1.17 | 244 | 8 |
| Nonanolide-1,4 | 92 | 0.87 | 156 | 5 |
| i-Nonyl acetate | 50 | 0.83 | 186 | 4 |
| i-Nonyl formate | 19 | 1.49 | 172 | 8 |
| Phenylethyl phenyl acetate | 0 | 1.22 | 241 | 7 |
| Class 6 - Alcohols & Ethers | | | | |
| Cinnamic alcohol | — | 1.28 | 134 | 9 |
| Dimyrcetol | 16 | 1.22 | 156 | 9 |
| 1,3,4,6,7,8-Hexahydro-4,6,6,7,8,8-hexamethyl cyclopenta-α-2-benzopyran (Galaxolide) | 100 | — | 240 | 5 |
| Hydroxymethyl isopropyl cyclopentane | 60 | 1.23 | 142 | 8 |
| 3a-Methyl-dodecahydro-6,6,9a-trimethylnaphtho-2(2,1-b)furan | 58 | 1.30 | 230 | 5 |
| Tetrahydromuguol | 24 | 1.23 | 158 | 8 |

Examples of perfume ingredients that are not bleach-stable, (which accordingly are not likely to contribute substantially to the deodorant properties of the perfume when formulated in the presence of bleach materials) are as follows:

| | LIC value | RVR value | m | BST panel score |
|---|---|---|---|---|
| Benzoin Siam resinoids | 87 | — | — | 14 |
| Benzyl salicylate | 0 | 1.58 | 228 | 17 |
| Bergamot AB 37 | 58 | 0.97 | 175 | 10 |
| p-t-Butyl cyclohexyl acetate | 54 | 0.98 | 198 | 10 |
| p-t-Butyl-α-methyl hydrocinnamic aldehyde (Lilial) | 74 | — | 204 | 13 |
| Coumarin | 58 | 1.22 | 146 | 10 |
| Ethyl vanillin | 100 | 1.43 | 152 | 12 |
| Geranium oil Bourbon | 26 | 1.29 | 154 | 10 |
| LRG 201 (a well known resorcylic acid ester) | 100 | 1.21 | 196 | 11 |
| Mousse de chene Yugo | 98 | 1.29 | 182 | 11 |
| β-Naphthyl methyl ether | 100 | — | 158 | 11 |
| Opoponax resinoid | 96 | 1.33 | 150 | 11 |
| Patchouli oil | 76 | 1.25 | 140 | 11 |
| Petitgrain oil | 34 | 1.27 | 175 | 11 |
| Phenylethyl alcohol | 22 | 1.24 | 122 | 10 |
| Pimento leaf oil | 100 | — | 165 | 12 |
| Pomeransol AB 314 | 100 | — | — | 11 |

Of the components and ingredients listed herein, those that are preferred for their relatively milder odour intensity are (a) the ingredients included in the examples given below, and (b)

Bergamot AB,

Hexyl salicylate,

Rose AB 380,

Diethyl phthalate,

Nonanediol 1,3-diacetate,

Isononyl acetate,

Cinnamic alcohol,

Benzoin Siam resinoid,

Benzyl salicylate, p-t-butyl-alpha-methyl-hydrocinnamic aldehyde,

Opoponax resinoid.

A deodorant perfume should contain at least five different components, and from preferably at least four of the classes, preferably five or six. It is however possible, and indeed is usually advantageous, to employ more than five different components when formulating the perfume. Ideally, most if not all of the perfume is formulated from deodorant perfume components.

Components present in the deodorant perfume for purposes other than obtaining a deodorant effect, for example an adjunct like an anti-oxidant, may be excluded from the operation of the preceding instructions to the extent that the component is required for that other purpose. The levels at which adjuncts are conventionally present in perfumes or in products to which perfumes are added is well-established for conventional materials and readily determinable for new materials so that the application of the above exclusion presents no difficulty.

ODOUR INTENSITY INDEX METHOD

The samples are assessed by a panel of a suitable number, e.g. about 34, of assessors who have been trained to score the intensity of a sample using the magnitude estimation technique. This is a ratio scaling method in which the relative intensity of each sample is scored in ratio to the intensities of a range of odour standards (here, benzyl acetate diluted in dipropylene glycol at various concentrations.

1.5 g (+/− 0.1 g) of perfume, or 1.5 g (+/−0.1 g) of benzyl acetate either neat or as a dilution in dipropylene glycol, is placed into 7 ml white soda S. N. B. screw neck vials with 19 mm diameter necks. The samples are each coded and presented to the panel in a random order at least twice. A total of at least 64 assessments (or enough to reach statistical significance) is made for each sample by at least 16 panellists on each day over two days. Assessments are made in environmentally controlled assessment rooms using coloured lighting to ensure that panellists are not influenced by any slight colour differences between the samples.

Individual assessments are normalised and averaged to give a consensus intensity rating for each sample. The perceived intensities are expressed in arbitrary units and are derived from consensus magnitude estimates which are indicative of the ratio of perceived intensities, as follows:

Each panellist was required to assess the intensity of a control sample (10% benzyl acetate solution in dipropylene glycol) in addition to each test fragrance and the reference samples. The intensity value (magnitude estimate) of the control sample was then used to normalise all the other assessments for each panellist as follows:

$$\text{Normalised Intensity} = \frac{\text{Intensity of Unknown}}{\text{Intensity of control}} \times 100.$$

or:

$$(I_N)_j = \frac{(i_K)_j}{(i_c)_j} \times 100$$

The normalised values for a sample were combined across all panellists to give a consensus value for the whole panel (the arithmetic mean).

$$\text{Odour intensity index} = \Sigma \frac{\text{(normalised panellist ratings)}}{\text{number of panellists.}}$$

or:

$$I_K = \sum_1^J \frac{(I_N)_j}{J}$$

KEY $I_K$=odour intensity index for sample k for the whole panel.

$(i_K)_j$ odour intensity of sample (magnitude estimate) as reported by j'th panellist.

$(I_N)_j$ single panellist's normalised datum.

n=number of samples.

J=number of panellists

K=sample number.

$(i_c)_j$=odour intensity of control (magnitude estimate) as reported by j'th panellist.

The invention is further illustrated by the following non-limitative examples.

EXAMPLE 1

A fragrance composition suitable for use in this invention is formulated as follows:

| % | Component |
|---|---|
| 2.0 | Cedar wood oil (Virginian) |
| 2.0 | Cinnamic Alcohol |
| 13.0 | Diethyl Phthalate |
| 5.0 | Galaxolide DEP (50:50 mixture with diethyl phthalate) |
| 4.0 | Geranyl Phenylacetate |
| 1.0 | Guaiacwood oil (rectified) |
| 4.0 | Linalyl Benzoate |
| 6.0 | Moss Base AB 7004 (*) |
| 3.0 | Phenylethyl Phenylacetate |
| 20.0 | Rose Base AB 7003 (*) |
| 40.0 | Traseolide (Quest) |
| 100.0 | |

(*) (available from Quest International)

The odour type of this formulation is mildly floral, mossy, rose, and musk. The composition is of low odour intensity and is suitable for incorporation into (inter alia) fabric—washing detergent compositions for example at a rate of incorporation of about 0.2% by weight of the detergent formulation.

EXAMPLE 2

A further fragrance composition according to the invention is as follows:

| % | Component |
|---|---|
| 8.0 | Benzyl Alcohol |
| 7.5 | Benzyl Salicylate |
| 2.0 | Cedar wood oil (Virginian) |
| 20.0 | Galaxolide DEP |
| 1.0 | Grisalva (10% solution in dipropylene glycol) (IFF) |
| 5.0 | Hercolyn D (Hercules) |
| 3.0 | Isobutyl Benzoate |
| 2.0 | Isobutyl Cinnamate |
| 1.0 | Linalyl Cinnamate |
| 5.0 | Moss Base AB 7004 (*) |
| 20.0 | Muguet Base AB 7001 (*) |
| 5.0 | Tonalid (7-acetyl-1,1,3,4,4,6-hexamethyl-tetrahydronaphthalene) (Polak's Frutal Works) |
| 20.0 | Traseolide (*) |
| 100.0 | |

The odour type of this formulation is mildly woody, mossy, muguet and musk.

EXAMPLE 3

A further and highly preferred composition for extremely low odour intensity is as follows:

| % | Component |
|---|---|
| 5.0 | Benzyl Alcohol |
| 4.0 | Benzyl Cinnamate |
| 20.0 | Benzyl Salicylate |
| 1.0 | Cinnamyl Cinnamate |
| 5.0 | Diethyl Phthalate |
| 8.0 | Galaxolide DEP |
| 20.0 | Jasmin AB 7002 (*) |
| 5.0 | Linalyl Cinnamate |
| 2.0 | Sandalone AC 802 (*) |
| 30.0 | Traseolide (*) |
| 100.0 | |

The odour type of this formulation is mildly sweet, floral and musk.

EXAMPLE 4

A further example of a perfumery composition IN accordance with the invention is as follows:

| % | Component |
|---|---|
| 18.0 | Benzyl Salicylate |
| 2.0 | Diethyl Phthalate |
| 5.0 | Ethylene Brassylate |
| 10.0 | Galaxolide DEP |
| 20.0 | Muguet AB 7001 (*) |
| 2.0 | Phenylethyl Salicylate |
| 2.0 | Sandalone AC 802 (*) |
| 3.0 | Sandela (Givaudan) |
| 38.0 | Traseolide (*) |
| 100.0 | |

The odour type of this formulation is mildly muguet and musk.

EXAMPLE 5

A further example of a composition according to the invention is as follows:

| % | Component |
|---|---|
| 5.0 | Benzyl Alcohol |
| 8.0 | Benzyl Benzoate |
| 5.0 | Benzyl Cinnamate |
| 5.0 | Carnation AB 7005 (*) |
| 2.0 | Copaiba Balsam |
| 10.0 | Galaxolide DEP |
| 15.0 | Hexyl Salicylate |
| 15.0 | Jasmin Base AB 7002 (*) |
| 35.0 | Traseolide (*) |
| 100.0 | |

The odour type of this formulation is mildly spicy, jasmin and musk.

Odour Intensity Indices

The odour intensity indices of the above-cited examples are as follows:

| Composition | Odour Intensity Index |
|---|---|
| Example 1 | 87 |
| Example 2 | 85 |
| Example 3 | 72 |
| Example 4 | 79 |
| Example 5 | 75 |

For comparison and calibration, standard preparations of benzyl acetate have odour intensity indices as follows:

| Reference Standard | Perceived Odour Index |
|---|---|
| 1% Benzyl Acetate | 54 |
| 5% Benzyl Acetate | 89 |
| 10% Benzyl Acetate | 102 |
| 20% Benzyl Acetate | 108 |
| 50% Benzyl Acetate | 120 |
| Neat Benzyl Acetate | 132 |

(The standard samples of benzyl acetate are presented as dilutions in dipropylene glycol.)

The invention is susceptible of many modifications and variations as will be apparent to the skilled reader, and extends to all combinations and subcombinations of the features mentioned or described herein, and in the documents incorporated herein by reference as noted above.

We claim:

1. In a fabric meaning liquid or solid composition include, from 0.1% to 5% of a perfume composition of fragrance materials, the improvement wherein the content of fragrance materials in the perfume composition comprises (a) about 20% to 60% of at least one musk, based on the weight of the perfume composition, (b) at least 10% of at least one salicylate, based on the weight of the perfume composition on, and (c) at least about 20% of other fragrance materials which are neither musk nor salicylate, based on the weight of the perfume composition, and wherein the fragrance materials (a), (b) and (c) together have an odour intensity not greater than that of a 10% solution of benzyl acetate in dipropylene glycol.

2. Fabric treating composition according to claim 1 wherein said musk is selected from the group consisting of: 1,3,4,6,7,8-hexahydro- 4,6,6,7,8,8-hexamethylcyclopenta-2-benzopyran; 6-acetyl- 1-isopropyl-2,3,3,5-tetramethylindane; cyclohexadecen-7-olide; 4-acetyl- 6-tert-butyl-1,1-dimethylindane; cyclohexadecanolide; ethylene brassylate; cyclo- 1,13-ethylenedioxy-tridecan-1,13-dione; cyclopentadecanolide; cyclopentadecanone; 1,1,3,3,5-pentamethyl-4, 6-dinitroindane; 2-4-dinitro- 3-methyl-6-tert-butylanisole; 4-tert-butyl-3,5-dinitro-2,6-dimethylacetophenone; ethylene 1,12-dodecanedioate; 11-oxahexadecanolide; 2-tert-butyl-1, 3-dinitro-4,5,6-trinitrobenzene; 1-tert-butyl- 3,5-dimethyl-2, 4,6-trinitrobenzene; 5-acetyl-1,1,2,3,3,6-hexamethylindane; 1,1,2,4,4,7-hexamethyl-6-acetyl-1,2,3,4-tetrahydronaphthalene; and 1,1,4,4-tetramethyl-6-acetyl-7-ethyl-1,2,3,4-tetrahydronaphthalene.

3. A fabric treating composition according to claim 2 wherein said musk is selected from the group consisting of 1,3,4,6,7,8-hexahydro-4,6,6,7,8,8-hexamethylcyclopenta-2-benzopyran; 6-acetyl-1-isopropyl-2,3,3,5-tetramethylindane and 1,1,2,4,4,7-hexamethyl-6-acetyl-1,2,3,4-tetrahydronaphthalene.

4. A composition according to claim 1 which is a detergent composition suitable for fabric washing, comprising a detergent surfactant, and containing from 0.1% to 0.8% of said perfume composition.

5. A composition according to claim 1 having a Malodor

Reduction Value of at least 0.25 or an Odor Reduction Value of at least 0.25.

6. A composition according to claim 1 wherein said musk is selected from the group consisting of: 1,3,4,6,7,8-hexahydro-4,6,6,7,8,8-hexamethylcyclopenta-2-benzopyran, 6-acetyl- 1-isopropyl-2,3,3,5-tetramethylindane, cyclohexadecen-7-olide, 4-acetyl- 6-tert-butyl-1,1-dimethylindane, cyclohexadecanolide, ethylene brassylate, cyclo-1,13-ethylenedioxytridecan- 1,13-dione, cyclopentadecanolide, cyclopentadecanone, 1,1,3,3,5-pentamethyl- 4,6-dinitroindane, 2,4-dinitro-3-methyl-6-tert-butylanisole, 4-tert-butyl- 3,5-dinitro-2,6-dimethylacetophenone, ethylene 1,12-dodecanedioate, 11-oxahexadecanolide, 2-tert-butyl-1,3-dinitro-4,5-trinitrobenzene, 1-tert-butyl-3,5-dimethyl- 2,4,6-trinitrobenzene 5-acetyl-1,1,2,3,6-hexamethylindane, 1,1,2, 4,4,7-hexamethyl- 6-acetyl-1,2,3,4-tetrahhydronaphthalene, and 1,1,4,4-tetramethyl-6-acetyl-7-ethyl- 1,2,3,4-tetrahydronaphthalene, and a balance of non-musk fragrance materials which include at least one salicylate, the amount of salicylate being at least 10% by weight of the composition, the composition having an odor intensity not greater than that of 10% solution of benzyl acetate in dipropylene glycol.

7. A composition according to claim 6 wherein said at least one musk provides at least 0.02% of the fabric-treating compositon.

8. A composition according to claim 6 wherein the perfume composition has a Malodor Reduction Value of at least 0.25 or an Odor Reduction Value of at least 0.25.

9. A composition according to claim 1 containing from 0.1% to 0.8% of said perfume composition.

10. A composition according to claim 1 which is a sheet-form solid fabric conditioning composition containing from 2% to 4% of said perfume composition.

11. A composition according to claim 1 wherein the content of fragrance materials in the perfume composition comprises (a) about 30% to 60% of said at least one musk and (c) at least about 30% of said other fragrance materials which are neither musk nor salicylate, based on the weight of the perfume composition.

* * * * *